United States Patent [19]

Zirnstein et al.

[11] Patent Number: 5,914,072
[45] Date of Patent: Jun. 22, 1999

[54] PHOSPHORIC ESTERS

[75] Inventors: Michael Zirnstein, Schriesheim; Jörg Schröder, Weinheim; Robert Kreuzer, Ludwigshafen, all of Germany

[73] Assignee: BASF Aktiengesellschaft, Ludwigshafen, Germany

[21] Appl. No.: 08/691,317

[22] Filed: Aug. 2, 1996

[30] Foreign Application Priority Data

Aug. 9, 1995 [DE] Germany .......................... 195 29 242

[51] Int. Cl.$^6$ .............................. B01F 17/14; C08K 5/521
[52] U.S. Cl. ........................ 252/356; 525/415; 528/354; 528/361; 106/503; 516/57; 516/908
[58] Field of Search ..................................... 252/351, 356, 252/357, 525, 452, 437, 415; 106/503; 528/272, 287, 354, 361, 59, 65, 80; 516/13, 40, 199, 908, 57

[56] References Cited

U.S. PATENT DOCUMENTS

| | | | |
|---|---|---|---|
| 4,098,741 | 7/1978 | Login ........................ | 528/287 |
| 4,111,816 | 9/1978 | Login ........................ | 528/287 |
| 4,229,554 | 10/1980 | Newkirk et al. .......... | 525/438 |
| 4,421,602 | 12/1983 | Brunnmueller et al. .............. | 162/168.2 |
| 4,459,220 | 7/1984 | Bellos ........................ | 252/344 |
| 4,720,514 | 1/1988 | Needham ................ | 523/351 |
| 4,746,462 | 5/1988 | Nakamura et al. ...... | 558/180 |
| 4,872,916 | 10/1989 | Latosky ................... | 106/503 |
| 4,986,851 | 1/1991 | Dietz et al. .............. | 106/503 |
| 5,130,463 | 7/1992 | Haubennestel et al. ................. | 558/172 |
| 5,300,255 | 4/1994 | Campbell et al. ....... | 252/351 |
| 5,344,584 | 9/1994 | Verelst et al. ........... | 252/356 |

FOREIGN PATENT DOCUMENTS

| | | |
|---|---|---|
| 0 056 523 A2 | 7/1982 | European Pat. Off. . |
| 0 071 051 A1 | 2/1983 | European Pat. Off. . |
| 0 256 427 A3 | 2/1988 | European Pat. Off. . |
| 0 256 454 A3 | 2/1988 | European Pat. Off. . |
| 0 417 490 A3 | 3/1991 | European Pat. Off. . |
| 0 555 950 A1 | 8/1993 | European Pat. Off. . |

OTHER PUBLICATIONS

Database WPIDS in STN, week 8830, London: Derwent Publications Ltd., AN 88–205617, Class A23, AU 86–65898 A (Horiguchi et al.) abstract, 1988.

*Primary Examiner*—Richard D. Lovering
*Assistant Examiner*—Daniel S. Metzmaier
*Attorney, Agent, or Firm*—Oblon, Spivak, McClelland, Maier & Neustadt, P.C.

[57] ABSTRACT

Phosphoric esters obtained by a) reacting a mono-, oligo- or polyamine with an alkylene oxide or alkylene carbonate to give an amino alcohol or amino mono-, oligo-, or polyether alcohol, from 50 to 100% of the alkoxylatable NH groups of the amine being alkoxylated, b) reacting the resulting amino (ether) alcohol with a hydroxycarboxylic acid or a dicarboxylic acid and a diol to give a mono-, oligo- or polyester, or reacting it with a diisocyanate and a diol to give a di-, oligo- or polyurethane, from 50 to 100% of the terminal hydroxyl groups in the amino (ether) alcohol being esterified or converted into urethane groups, and c) reacting the resulting amino (ether) ester or urethane with a phosphorus compound which forms phosphoric esters, from 5 to 100% of the terminal hydroxyl groups in the amino (ether) ester or urethane being converted into phosphoric ester groups, and the phosphorus atoms being mono- and/or di- and, if appropriate, tri-esterified, preparation of the phosphoric esters, and their use as dispersants for solids.

12 Claims, No Drawings

PHOSPHORIC ESTERS

The present invention relates to phosphoric esters which are obtainable by reacting a) reacting a mono-, oligo- or polyamine with an alkylene oxide or alkylene carbonate to give an amino alcohol or amino mono-, oligo- or polyether alcohol, from 50 to 100% of the alkoxylatable NH groups of the amine being alkoxylated, b) reacting the resulting amino (ether) alcohol with a hydroxycarboxylic acid or a dicarboxylic acid and a diol to give a mono-, oligo- or polyester, or reacting it with a diisocyanate and a diol to give a di-, oligo- or polyurethane, from 50 to 100% of the terminal hydroxyl groups in the amino (ether) alcohol being esterified or converted into urethane groups, and c) reacting the resulting amino (ether) ester or urethane with a phosphorus compound which forms phosphoric esters, from 5 to 100% of the terminal hydroxyl groups in the amino (ether) ester or urethane being converted into phosphoric ester groups, and the phosphorus atoms being mono- and/or di- and, if appropriate, triesterified.

The invention additionally relates to the preparation of the phosphoric esters and to their use as dispersants for solids.

In order to facilitate and improve the dispersion of solids in liquid media, it is common to employ dispersants which should at the same time also have a stabilizing effect on the resulting dispersions and should prevent reagglomeration or flocculation of the solid particles. As surface-active agents, the dispersants promote the wetting of the solid particles which are to be dispersed, and facilitate the breaking up of agglomerates.

They are particularly important, for example, for the dispersion of pigments in binders in the preparation of printing inks, paints and varnishes and in the pigmentation of plastics compositions. For economic reasons attempts are made in this context to start from very highly concentrated pigment dispersions, for example stock pastes in the production of paints and printing inks, or masterbatches in the pigmentation of plastics, which can be adjusted to appropriate viscosities only with the aid of dispersants.

The use of acidic phosphoric esters of various structures as dispersants for pigments is known from a variety of publications. For instance, U.S. Pat. No. 4 720 514 describes phosphoric esters based on alkoxylated alkyl(nonyl)phenols for this purpose. EP-A-56 523 and 555 950 and U.S. Pat. No. 4 872 916 disclose phosphoric esters based on ethoxylated aromatic alcohols, and EP-A-256 427 phosphoric esters based on ethoxylated fatty alcohols, as pigment dispersants for aqueous systems. Furthermore, EP-A-256 454 describes pigment-dispersing phosphoric esters based on polyesters which have terminal hydroxyl groups and are prepared by polycondensation of polycarboxylic acids and polyalcohols, while EP-A-417 490 describes those based on likewise hydroxyl-terminated, alkoxylated and esterified monoalcohols (alkyl polyethylene glycol polyesters).

However, the known dispersants have the disadvantage that in most cases they cannot be employed universally and that in various binder systems, for example in waterborne systems and high-solids systems, they exhibit an inadequate dispersing action and therefore lead to poor transparency and losses in gloss in the coatings prepared, or are even incompatible with the binder systems. Moreover, these acidic phosphoric esters generally require a basic amine additive, which is undesirable in the quantity required, in order to establish, for example, the optimum pH of a coating system. Already (partially) neutralized salts of these esters often contain volatile amines which lead to odor pollution.

It is therefore an object of the invention to provide dispersants having advantageous performance properties, which can readily be adapted to the respective media.

We have found that this object is achieved by the phosphoric esters defined at the outset.

We have also found that these phosphoric esters can be prepared by the process hereby defined.

We have also found that the phosphoric esters can be used as dispersants for solids.

An essential feature of the novel phosphoric esters is that, owing to the basic amino groups and acidic phosphoric acid radicals also present, they are at least partially neutralized in the form of inner salts (ammonium cation/phosphate anion) and therefore require little or no addition of amine when used in binder systems, and especially for varnishes.

The novel phosphoric esters can advantageously be obtained by the novel preparation process, in which a) an amine is reacted with an alkylene oxide or alkylene carbonate to form an amino alcohol or amino ether alcohol, b) the resulting amino alcohol or amino ether alcohol is esterified with a hydroxycarboxylic acid or a dicarboxylic acid and a diol, or is converted into a urethane with a diisocyanate and a diol, and c) the resulting amino ester or amino ether ester or the resulting amino urethane or amino ether urethane is converted into a phosphoric ester (phosphatized).

Suitable amine components in step a) are not only ammonia but also, in particular, primary and, very particularly, secondary amines (in this context one primary amino group means two alkoxylatable NH functions). Preference is given in this context to aliphatic and cycloaliphatic amines which may be unsaturated but are preferably saturated. Also suitable are araliphatic and aromatic amines, which may contain monocyclic or polycyclic aryl radicals or biphenyl radicals. The alkyl radicals in the amines can be linear or branched, and the aliphatic and aromatic rings can be substituted by alkyl or alkoxy of preferably 1 to 30 carbon atoms.

It is also possible to employ both monoamines and oligoamines (which term is intended to include diamines and triamines) and polyamines, such as polyalkylenepolyamines and polyvinylamines, but preferably those amines containing only one alkoxylatable NH group, especially secondary monoamines having different or, preferably, identical alkyl or cycloalkyl radicals.

Suitable aliphatic and araliphatic monoamines generally contain 1 to 30, preferably 2 to 24 carbon atoms. Aliphatic oligoamines generally have 1 to 20, especially 2 to 14, carbon atoms per alkylene radical, it being possible for the secondary or tertiary amine nitrogen atoms they contain to be substituted by alkyl, aralkyl and/or aryl radicals having 1 to 30, preferably 3 to 24, carbon atoms.

The amines can be functionalized further, for example alkoxylated (ether amines, polyether amines, polyether polyamines).

It is of course also possible to employ amino alcohols or amino ether alcohols directly, which, based on the amino, ether and alcohol functions, may in each case be either monovalent or polyvalent. The amino alcohols are preferably alkoxylated further to give amino ether alcohols; however, they can also be esterified, or-converted into a urethane, directly.

The following list gives examples of the individual amine components suitable:

aliphatic (including cycloaliphatic and araliphatic) monoamines:

methylamine, ethylamine, propylamine, isopropylamine, cyclopropylamine, butylamine, isobutylamine, sec-butylamine, tert-butylamine, pentylamine, 3-methylbutylamine, cyclopentylamine, hexylamine, cyclohexylamine, octylamine, 1,5-dimethylhexylamine, 2-ethylhexylamine, 3-aminomethylpinane, decylamine, dodecylamine, isotridecylamine, coconut fatty amine, palm fatty amine, hexadecylamine, octadecylamine, tallow fatty amine, hydrogenated tallow fatty amine, oleylamine, behenylamine, isonorbornylamine, benzylamine, 4-methoxybenzylamine, 1- and 2-phenylethylamine, 2- and 4-methoxyphenylamine, 3,4-dimethoxyphenylethylamine and 1-methyl-3-phenylpropylamine;

dimethylamine, N-methylethylamine, diethylamine, N-methylpropylamine, N-ethylpropylamine, N-ethylisopropylamine, dipropylamine, diisopropylamine, N-methylbutylamine, N-ethylbutylamine, dibutylamine, diisobutylamine, N-isobutyl-sec-butylamine, di-sec-butylamine, dipentylamine, diisopentylamine, pyrrolidine, N-methyl-cyclohexylamine, N-ethylcyclohexylamine, N-isopropylcyclohexylamine, N-butylcyclohexylamine, dicyclohexylamine, dihexylamine, piperidine, N-methyl-2-ethylhexylamine, N-butyl-2-ethylhexylamine, dioctylamine, di-2-ethylhexylamine, dicoconut fatty amine, distearylamine, dioleylamine, ditallow fatty amine, hydrogenated ditallow fatty amine and N-methylbenzylamine;

aliphatic oligoamines (including diamines and triamines):
1,2-diaminoethane, N-methyl-1,2-diaminoethane, N,N-dimethyl-1,2-diaminoethane, N,N'-dimethyl-1,2-diaminoethane, N,N,N'-trimethyl-1,2-diaminoethane, N-ethyl-1,2-diaminoethane, N,N-diethyl-1,2-diaminoethane, N,N'-diethyl-1,2-diaminoethane, N,N,N'-triethyl-1,2-diaminoethane, N-methyl-N'-ethyl-1,2-diaminoethane, N-methyl-N'-ethyl-1,2-diaminoethane, N,N-dimethyl-N'-ethyl-1,2-diaminoethane, N,N'-dimethyl-N-ethyl-1,2-diaminoethane, N-propyl-1,2-diaminoethane, N,N-dipropyl-1,2-diaminoethane, N,N'-dipropyl-1,2-diaminoethane, N,N,N'-tripropyl-1,2-diaminoethane, N-butyl-1,2-diaminoethane, N,N-dibutyl-1,2-diaminoethane, N,N'-dibutyl-1,2-diaminoethane, N,N,N'-tributyl-1,2-diaminoethane, 1,3-diaminopropane, N-methyl-1,3-diaminopropane, N,N'-dimethyl-1,3-diaminopropane, N,N-dimethyl-1,3-diaminopropane, N,N-diethyl-1,3-diaminopropane, N-ethyl-1,3-diaminopropane, N-propyl-1,3-diaminopropane, N,N-dipropyl-1,3-diaminopropane, N-cyclohexyl-1,3-diaminopropane, 2-ethylhexyl-1,3-diaminopropane, N-lauryl-1,3-diaminopropane, N-coconut fatty alkyl-1,3-diaminopropane, N-stearyl-1,3-diaminopropane, N-oleyl-1,3-diaminopropane, N-tallow fatty alkyl-1,3-diaminopropane, 4,4'-diaminocyclohexylmethane, 1,2-diaminopropane, N,N-dimethyl-1,2-diaminopropane, 1,4-diaminobutane, 1,2-diaminobutane, 1,3-diaminobutane, 1-diethylamino-4-aminopentane, 1,5-diaminopentane, neopentanediamine, dimethylneopentanediamine, 1,6-diaminohexane, N,N-diethyl-1,4-diaminobutane and isophoronediamine;

diethylenetriamine, N-methyldiethylenetriamine, N-ethyldiethylenetriamine, N-propyldiethylenetriamine, N-butyldiethylenetriamine, N,N-aminoethylmethylamine, N,N-aminoethylethylamine, N,N-aminopropylpropylamine, N,N-dimethyldiethylenetriamine, N,N-diethyldiethylenetriamine, N-ethyl-N-propyldiethylenetriamine, N,N-dipropyldiethylenetriamine, N,N-dibutyldiethylenetriamine, N,N''-dimethyldiethylenetriamine, N-methyl-N'-ethyldiethylenetriamine, N-ethyl-N'-methyldiethylenetriamine, N-methyl-N'-propyldiethylenetriamine, N-Propyl-N'-methyldiethylenetriamine, N,N'-diethyldiethylenetriamine, N,N''-dipropyldiethylenetriamine, N,N'-dibutyldiethylenetriamine, N,N''-dimethyldiethylenetriamine, N-methyl-N''-ethyldiethylenetriamine, N-methyl-N''-propyldiethylenetriamine, N,N''-diethyldiethylenetriamine, N,N'-dipropyldiethylenetriamine, N,N''-dibutyldiethylenetriamine, N,N,N'-trimethyldiethylenetriamine, N,N-dimethyl-N'-ethyldiethylenetriamine, N,N'-dimethyl-N-ethyldiethylenetriamine, N,N,N'-triethyldiethylenetriamine, N,N-diethyl-N'-methyldiethylenetriamine, N,N-dipropyl-N'methyldiethylenetriamine, N,N-dibutyl-N'-methyldiethylenetriamine, N,N,N''-trimethyldiethylenetriamine, N,N-dimethyl-N''-ethyldiethylenetriamine, N,N'-dimethyl-N''-ethyldiethylenetriamine, N,N,N''-triethyldiethylenetriamine, N,N-diethyl-N''-methyldiethylenetriamine, N,N-dipropyl-N''-methyldiethylenetriamine, N,N-dibutyl-N''-methyldiethylenetriamine, N-(2-aminoethyl)-1,3-diaminopropane, dipropylenetriamine, hexamethylenetriamine, N-methyldipropylenetriamine, N,N-dimethyldipropylenetriamine, N-ethyldipropylenetriamine, N-propyldipropylenetriamine, N-butyldipropylenetriamine, N-coconut fatty alkyldipropylenetriamine, N-tallow fatty alkyldipropylenetriamine, N-oleyldipropylenetriamine, N,N-bis(3-aminopropyl)methylamine, N,N-bis(3-aminopropyl)ethylamine, N,N-bis(3-aminopropyl)propylamine, N,N-bis(3-aminopropyl)laurylamine, N,N-bis(3-aminopropyl)coconut fatty alkylamine, N,N-bis(3-aminopropyl)tallow fatty alkylamine, N,N-dimethyldipropylenetriamine, N,N-diethyldipropylenetriamine, N,N-dilauryldipropylenetriamine, N,N-dicoconut fatty alkyldipropylenetriamine, N,N-ditallow fatty alkyldipropylenetriamine, N,N-dioleyldipropylenetriamine, N,N'-bis(3-aminopropyl)-1,6-diaminohexane and 1-bis(3-aminopropyl)-4-methylpiperazine;

N,N'-bis(3-aminopropyl)ethylenediamine, N,N'-bis(3-aminopropyl)butylenediamine, N,N'-bis(2-aminoethyl)piperazine, N,N'-bis(3-aminopropyl)piperazine, trisaminopropylamine, tetraethylenepentamine and tetrapropylenepentamine;

aliphatic polyamines:
  polyalkylenepolyamines such as poly(1,3- and/or 1,2-)-propylene- and poly(1,4-, 1,3- and/or 1,2-)-butylene-polyamines, and especially polyethylenepolyamines (polyethyleneimines) having a mean molecular weight $\overline{M}_n$ of in general from 200 to 3000, preferably 300 to 1000 (obtainable for example by polymerizing ethyleneimine in the presence of alkyl halides or acids as catalyst); are branched and contain primary and tertiary and/or secondary amino gorups (usually from 1 to 75 mol %, preferably from 30 to 50 mol % of primary, from 0 to 99 mol %, preferably from 30 to 50 mol %, of secondary, and from 1 to 50 mol %, preferably from 15 to 30 mol %, of tertiary amino groups, based on the total number of amino groups); partially or almost completely alkylated (usually $C_1$–$C_{20}$-alkyl, preferably $C_1$–$C_4$-alkyl) and/or acylated (usually $C_1$–$C_{20}$-alkanoyl) polyalkylenepolyamines having at least one alkoxylatable amino group;
  polyvinylamines having a mean molecular weight $\overline{M}_n$ of in general from 300 to 5000 (obtainable by polymerizing N-vinylcarboxamides and subsequent partial or complete hydrolytic elimination of the acyl groups; eg. EP-A-71 050);
aromatic mono- and diamines:
  aniline, 1- and 2-naphthylamine, o-phenylenediamine and 1,5- and 1,8-diaminonaphthalene;
ether amines, polyether amines and polyether polyamines:
  2-methoxyethylamine, 2-ethoxyethylamine, 1-methoxy-2-aminopropane, 2- and 3-methoxypropylamine, 3-ethoxypropylamine, morpholine, N-(3-aminopropyl)morpholine, 3-(2-ethylhexoxy)-propylamine, 3-decyloxypropylamine, 3-aminopropylethoxystearylamine, 3-(2-methoxyethoxy)propylamine, 3-oxapentane-1,5-diamine, 4-oxaheptane-1,7-diamine, 4,7-dioxadecane-1,10-diamine, 4,9-dioxadodecane-1,12-diamine, 4,11-dioxatetradecane-1,14-diamine and 4,7,10-trioxadecane-1,13-diamine;
  polyethylene glycol (3-aminopropyl) butyl ethers, polyethlyene glycol (3-aminopropyl) coconut fatty alkyl ethers, polyethylene glycol (2-aminoethyl) tallow fatty alkyl ethers, polyethylene glycol (3-aminopropyl) dodecyl ethers, bis(3-aminopropyl) polytetrahydrofurans and polyoxyethylenediamines and polyoxypropylenediamines having a mean molecular weight $\overline{M}_n$ of in general from 150 to 3000, preferably from 300 to 1500;
  polyoxyethylenepolyamines and polyoxypropylenepolyamines having a mean molecular weight $\overline{M}_n$ of in general from 150 to 3000, preferably from 300 to 1500;
amino alcohols, amino ether alcohols and polyamino polyether alcohols:
  ethanolamine, diethanolamine, triethanolamine, 2-methylaminoethanol, 2-dimethylaminoethanol, 2-ethylaminoethanol, 2-diethylaminoethanol, 2-diisopropylaminoethanol, 2-butylaminoethanol, 2-Cyclohexylaminoethanol, 2-dibutylaminoethanol, N-butyldiethanolamine, N-methyldiethanolamine, N-(2-hydroxyethyl)-1,2-diaminoethane, N,N- and N,N'-bis(2-hydroxyethyl)-1,2-diaminoethane, N,N, N'-tris(2-hydroxyethyl)-1,2-diaminoethane, N,N,N', N'-tetrakis(2-hydroxyethyl)-1,2-diaminoethane, 2-(2-aminoethylamino)-ethanol, N-(2-hydroxyethyl)-1,2-diaminopropane, N,N- and N,N'-bis(2-hydroxyethyl)-1,2-diaminopropane, N,N,N'-tris(2-hydroxyethyl)-1,2-diaminopropane, N,N,N', N'-tetrakis(2-hydroxyethyl)-1,2-diaminopropane, N-(2-hydroxyethyl)-1,3-diaminopropane, N,N- and N,N'-bis(2-hydroxyethyl)-1,3-diaminopropane, N,N,N'-tris(2-hydroxyethyl)-1,3-diaminopropane, N,N,N',N'-tetrakis(2-hydroxyethyl)-1,3-diaminopropane, 2-aminopropanol, isopropanolamine, 2-dimethylaminopropanol, 1-dimethylaminoisopropanol, 1-ethylaminoisopropanol, diisopropanolamine, triisopropanolamine, N-methyldiisopropanolamine, 3-amino-2,2-dimethylpropanol, 3-(2-hydroxyethylamino)isopropanol and 2-aminobutanol;
  2-(2-aminoethoxy)ethanol, 2-(2-dimethylaminoethoxy)ethanol, aminopropylethoxystearyl alcohol and aminoethylethoxy-coconut fatty alcohol;
  polyetherpolyamines which are obtainable by condensation of diethanolamine or triethanolamine and have a mean molecular weight $\overline{M}_n$ of in general from 250 to 300 (U.S. Pat. No. 4 459 220).

In general, the degree of reaction of the alkoxylatable NH groups of the amine in the alkoxylation step a) is from 50 to 100%, preferably 100%.

Suitable alkoxylating agents are alkylene carbonates and especially alkylene oxides, which in general have $C_2$–$C_8$-alkylene radicals, preferably $C_2$–$C_3$-alkylene radicals and, with particular preference, ethylene radicals, which can be substituted by aryl radicals, especially phenyl radicals, but are preferably unsubstituted.

Examples of suitable alkoxylating agents are ethylene carbonate, propylene carbonate, styrene oxide, butylene oxide, especially propylene oxide, and in particular ethylene oxide and mixtures thereof.

The numerical ratio of the resulting alkylene oxide units in the amino (ether) alcohols (and the novel phosphoric esters) to the alkoxylatable NH groups in this context is usuallyfrom 0.5:1 to 200:1, preferably from 1:1 to 150:1, particularly preferably from 2:1 to 100:1, and, with very particular preference, from 3:1 to 50:1.

For the numerical ratio of the ether oxygen atoms which are formed in the alkoxylation to the NH groups, comparable values apply. In an extreme case, however, it is possible for no ether oxygen atom to be present in the amino alcohols (and therefore in the novel phosphoric esters) if there is only one alkylene oxide unit per NH group.

The mean molecular weight $\overline{M}_n$ of the amino alcohols or amino ether alcohols is in general from 100 to 10,000.

Preference is given to amino ether alcohols containing only one terminal hydroxyl group.

In the process according to the invention, the alkoxylation step a) can be carried out in the manner which is customary for reactions with ethylene oxide and is described, for example, in N. Schnöfeldt, Grenzflächenaktive Ethylenoxid-Addukte, Wissenschaftliche Verlagsgesellschaft mbH, Stuttgart, 1st edition, pages 14 to 33 and 70–73 (1976) and supplement, page 33 to 35 (1984).

Preference is given to the two-step procedure in which the amine is first of all reacted with preferably from 0.8 to 1.2 mol of ethylene oxide per NH group to be reacted, in general at from 80 to 180° C., preferably from 110 to 160° C., in the presence of water as catalyst (in general from 0.5 to 10% by weight, preferably from 3 to 6% by weight, based on the amine to be ethoxylated), and then, after removal of the water, is reacted with the remaining quantity of ethylene oxide, usually at from 80 to 160° C., in particular 100 to 140° C., in the presence preferably of potassium hydroxide or else sodium hydroxide as catalyst (usually from 0.05 to 5% by weight, preferably from 0.2 to 1.5% by weight, based on the amine to be ethoxylated) until the desired degree of ethoxylation is reached. The catalyst is preferably added in the form of an aqueous solution, and the water is then preferably removed totally. Any polyethylene glycol formed can be removed after each of the two steps by washing with water or an aqueous solution of sodium chloride.

It is also possible to work in one step, by reacting the amine directly with an excess of ethylene oxide at from about 80 to 160° C., preferably from 100 to 140° C., in the presence of potassium hydroxide or else sodium hydroxide. A more controlled reaction regime, leading to purer products, however, is only possible with the two-step variant.

In step b) of the novel preparation process, the terminal hydroxyl groups in the resulting amino alcohol or amino ether alcohol are esterified or converted into urethane groups to the extent of in general from 50 to 100%, preferably completely. NH groups unreacted in step a) are in general amidated or converted into urea groups in this step.

Particularly suitable compounds for the esterification are hydroxycarboxylic acids and also mixtures of dicarboxylic acids and dialcohols. It is of course also possible, instead of the hydroxycarboxylic acids, to employ their esters, both the alkyl esters (especially $C_1$–$C_8$-alkyl esters, preferably methyl ester and ethyl ester) and internal esters (lactones) or intermolecular esters (lactides), and instead of the dicarboxylic acids to employ their esters (especially $C_1$–$C_8$-alkyl esters, preferably methyl ester and ethyl ester) and anhydrides (including cyclic anhydrides in particular).

The hydroxycarboxylic acids can be aliphatic, cycloaliphatic or aromatic.

Particularly suitable aromatic hydroxycarboxylic acids are hydroxy-substituted benzoic acids and naphthalenecarboxylic acids, such as p-hydroxyethylbenzoic acid and 2-hydroxynaphthalene-6-carboxylic acid.

Preference is given to aliphatic hydroxycarboxylic acids, especially those with hydroxyl groups in the ω position, and their lactones. In general the aliphatic hydroxycarboxylic acids have from 2 to 22 carbon atoms, preferably from 4 to 18 carbon atoms. Examples which may be mentioned are glycolic acid, lactic acid and its lactide, γ-hydroxybutyric acid and γ-butyrolactone, δ-hydroxyvaleric acid and γ- and δ-valerolactone, especially ε-hydroxycaproic acid and ε-caprolactone, 12-hydroxystearic acid and ricinoleic acid, and also mixtures, especially including naturally occurring acids.

Suitable dicarboxylic acids can likewise be aliphatic, cycloaliphatic or aromatic, with preference being given to saturated and unsaturated aliphatic dicarboxylic acids, their anhydrides and their esters, while aromatic dicarboxylic acids are derived in particular from phthalic acid. The aliphatic dicarboxylic acids generally contain from 2 to 22 carbon atoms, preferably from 4 to 14 carbon atoms.

Examples of suitable dicarboxylic acids are succinic acid and succinic anhydride, glutaric acid and glutaric anhydride, adipic acid, azelaic acid, sebacic acid, maleic acid and maleic anhydride, fumaric acid, decenylsuccinic anhydride, $c_{12/14}$- and $c_{16/18}$-alkenylsuccinic anhydrides, rosin/maleic anhydride adducts, hexahydrophthalic anhydride, tetrahydrophthalic anhydride, 3,6-endomethylenetetrahydrophthalic acid, methyl-3,6-endomethylenetetrahydrophthalic acid, phthalic acid and phthalic anhydride, isophthalic acid and terephthalic acid, and also mixtures thereof.

Suitable diols are not only aromatic and cycloaliphatic diols but also, in particular, aliphatic dialcohols (in general with 2 to 20, preferably 2 to 8, carbon atoms) and the adducts and polyadducts thereof, which lead to the formation of esters containing additional ether oxygen atoms, and also mixtures thereof, examples being ethylene glycol, diethylene glycol, triethylene glycol and polyethylene glycols ($\overline{M}_n$ of in general from 190 to 600), 1,2- and 1,3-propylene glycol, dipropylene glycols and polypropylene glycols ($\overline{M}_n$ of in general from 190 to 600), 1,3- and 1,4-butanediol and polytetramethylene glycols ($\overline{M}_n$ of in general from 150 to 1000), neopentyl glycol, hexamethylene glycol and octamethylene glycol.

The molar ratio of the components reacted in the presence of the amino (ether) alcohol, namely dicarboxylic acid and diol, is preferably chosen in this cotnext such that an essentially hydroxy-terminated ester of minimal acid number (in general ≦25 mg of KOH/g, preferably ≦10 mg of KOH/g, particularly preferably ≦3 mg of KOH/g) is obtained.

For the formation of urethanes, mixtures of diisocyanates and diols are employed whose molar ratio is likewise preferably such as to give an essentially hydroxy-terminated urethane.

Suitable diisocyanates are aliphatic and cycloaliphatic diisocyanates and also aromatic diisocyanates. Preference is given to alkylene diisocyanates which in general have from 2 t o 15 carbon atoms, especially 4 to 12 carbon atoms, in the alkylene chain.

Examples which may be mentioned are tetra- and hexamethylene diisocyanate, 1,3,5-trimethylhexamethylene diisocyanate, dodecamethylene diisocyanate, isophorone diisocyanate, methylenebis (4-cyclohexyl isocyanate), 1,4-cyclohexane bismethyleneisocyanate, tolylene diisocyanate and diphenylmethane diisocyanate.

Suitable diols are the compounds mentioned in the case of esterification.

The numerical ratio of the carboxylic ester groups in the resulting amino (ether) esters (and in the novel phosphoric esters) to the NH groups of the amine is usually from 1:1 to 150:1, preferably from 1:1 to 60:1 and, with particular preference, from 2:1 to 30:1. The amino (ether) urethanes are subject to the same numerical ratios, but there are at least 2 urethane groups per NH group.

The mean molecular weight $\overline{M}_n$ of the amino (ether) esters and urethanes is in general from 100 to 25,000, in particular from 250 to 15,000 and, very especially, from 250 to 6000.

Particular preference is given to amino ether esters (and the novel phosphoric esters) in which the NH groups in the amine are completely alkoxylated and esterified.

Among these amino ether esters, preference is given in turn to those containing only one terminal hydroxyl group.

In the novel process, the esterification step b) can be carried out as is generally customary for esterification and is described, for example, in Houben-Weyl, Methoden der organischen Chemie, 4th edition, volume XIV/2, pages 1 to 30 (1963).

Thus the esterification of the amino alcohol or amino ether alcohol with the hydroxycarboxylic acids can in general take place at from 80 to 250° C., preferably at from 120 to 200° C., advantageously in the presence of customary esterification catalysts such as organic metal salts or acids, for example titanium(IV) butylate, zirconium naphthenate, zinc acetate and p-toluenesulfonic acid (in general from 0.05 to 3% by weight, especially from 0.1 to 1% by weight, based on the overall quantity of reactants), or else without catalyst, with removal of the water of reaction in the presence or absence of an inert organic solvent which preferably forms azeotropes with water.

When acid lactones or lactides are used, the esterification—which proceeds as an addition or polyaddition reaction (ring-opening polymerization)—can be carried out at in general from 70 to 200° C., in particular from 120 to 160° C., likewise preferably in the presence of an esterification catalyst, for example dibutyltin dilaurate, tin dioxide or titanium tetrabutylate, in the presence or absence of an organic solvent.

It is of course also possible to react the amino alcohol or amino ether alcohol directly with polyesters prepared separately from the abovementioned carboxylic acids and, if appropriate, diols, preferably the hydroxycarboxylic acids or their lactones. In this case the polyesters should contain terminal hydroxyl groups and terminal carboxyl groups in a numerical ratio of in general from 1.1 to 0.8:1, preferably from 1.05 to 0.95:1.

Where urethanes are to be formed in step b) of the novel process, their preparation can likewise be carried out as is generally customary and is described, for example, in Houben-Weyl, Methoden der Organischen Chemie, 4th edition, volume XIV/2, page 57 ff. (1963).

In step c) of the novel preparation process, in general from 5 to 100% of the terminal hydroxyl groups in the resulting amino (ether) ester or urethane are phosphatized. The preferred degree of phosphatization depends in this case on the number of hydroxyl groups to be esterified and, in the case of only one hydroxyl group, is preferably from 50 to 100% and especially from 97 to 100%, in the case of 2 hydroxyl groups is preferably from 50 to 100% and especially from 97 to 100%, in the case of 3 hydroxyl groups is preferably from 35 to 70% and especially from 45 to 70%, in the case of 4 hydroxyl groups is preferably from 25 to 75% and especially from 35 to 75%, in the case of 5 hydroxyl groups is preferably from 20 to 60% and especially from 30 to 60%, and for more than 5 hydroxyl groups is preferably from 15 to 50% and especially from 20 to 50%.

Very particular preference is given to those novel phosphoric esters in which the NH groups in the amine are completely alkoxylated, esterified and phosphatized.

The numerical ratio of the phosphorus atoms to the NH groups of the amine in the novel phosphoric esters is in general from 0.05:1 to 3:1, preferably from 0.2 to 2:1 and with particular preference from 0.5:1 to 1.5:1.

The novel phosphoric esters are preferably primary or secondary esters. Mixtures of both forms are usually present, and may also contain tertiary esters.

The OH functions of less than tri-esterified phosphorus atoms are preferably in the form of free acid functions which, together with the amino nitrogen atoms present, lead to the formation of inner salts (zwitterionic compounds). However, they can also be neutralized by reaction with inorganic bases such as alkali metal hydroxides, for example sodium, potassium or lithium hydroxide, or alkaline earth metal hydroxides, for example magnesium or calcium hydroxide, and ammonia or organic bases such as mono-, di- or tri($C_1$–$C_6$-alkyl)amines, for example trimethylamine, triethylamine, diethylamine, dipropylamine, dibutylamine, or mono-, di- or tri($C_1$–$C_4$-alkanol)amines, for example ethanolamine, diethanolamine or triethanolamine, and in this case are in the form of the corresponding salts.

Examples of ester-forming phosphorus compounds suitable for the phosphatization c) are phosphorus oxychloride, orthophosphoric acid and, preferably, phosphorus pentoxide and polyphosphoric acids, especially linear polyphosphoric acids of the formula $H_{n+2}P_nO_{3n+1}$, in which n is preferably from 2 to 10 (low molecular weight polyphosphoric acids), a value of 5 being particularly preferred for n and corresponding to a polyphosphoric acid with a $P_4O_{10}$ content of 85%, both of which lead in particular to the formation of mixtures of primary and secondary phosphoric esters.

The reaction of the amino (ether) esters or urethanes formed in step b) with these phosphatizing agents can be carried out in accordance with methods which are known per se and are described, for example, in Houben-Weyl, Methoden der organischen Chemie, 4th edition, volume XII/2, pages 143–210 (1963).

The recommended temperatures for this reaction depend on the phosphorus compound: when phosphorus oxychloride is used they are for example from 20 to 130° C., from 80 to 180° C. in the case of orthophosphoric acid, and from 50 to 130° C., preferably from 70 to 110° C., in the case of polyphosphoric acid and phosphorus pentoxide.

In the course of phosphatization it is generally unnecessary to use solvent, with the phosphorus compound instead advantageously being introduced directly into a melt of the amino (ether) ester or urethane.

The quantity of phosphorus compound employed depends on the desired degree of phosphatization. The maximum quantity is determined by the mean number of hydroxyl groups in the amino (ether) ester or urethane, which can be determined by way of the hydroxyl number of the ester or urethane.

When the preferred agents, polyphosphoric acid and phosphorus pentoxide, are used, and especially when they are used in excess, di- and polyphosphoric esters may be formed, but these can readily be hydrolyzed in the presence of water to give the novel orthophosphoric esters.

The novel phosphoric esters can of course also be obtained by other methods, by first preparing a polyester from the hydroxycarboxylic acid or esters thereof, phosphatizing this polyester, and finally reacting the resulting phosphoric ester with the alkoxylated amine.

The novel phosphoric esters are advantageously suitable as dispersants for solids of all kinds. They are particularly suitable, for example, for the dispersion of fillers such as barytes, lime, kaolin and talc, for example in plastics, and are especially suitable for the dispersion of organic and inorganic pigments, both in plastics and, in particular, in varnishes, printing inks and paints. In this field they offer particular advantages for the dispersion of polar organic pigments and especially inorganic pigments, particularly iron oxide pigments.

Examples which may be mentioned of pigments to be dispersed are:

monoazo pigments:
    C.I. Pigment Brown 25;
    C.I. Pigment Orange 5, 36 and 67;
    C.I. Pigment Red 1, 2, 3, 48:4, 49, 52:2, 53, 57:1, 251, 112, 170 and 184;
    C.I. Pigment Yellow 1, 3, 73, 74, 65, 97, 151 and 183;
disazo pigments:
    C.I. Pigment Orange 34;
    C.I. Pigment Red 144 and 166;
    C.I. Pigment Yellow 12, 13, 17, 83, 113 and 126;
anthraquinone pigments:
    C.I. Pigment Yellow 147 and 177;
    C.I. Pigment Violet 31;
anthrapyrimidine pigments:
    C.I. Pigment Yellow 108;

quinacridone pigments:
: C.I. Pigment Red 122, 202 and 20;
: C.I. Pigment Violet 19;

quinophthalone pigments:
: C.I. Pigment Yellow 138;

dioxazine pigments:
: C.I. Pigment Violet 23 and 27;

flavanthrone pigments:
: C.I. Pigment Yellow 24;

indanthrone pigments:
: C.I. Pigment Blue 60 and 64;

isoindoline pigments:
: C.I. Pigment Orange 69;
: C.I. Pigment Red 260;
: C.I. Pigment Yellow 139;

isoindolinone pigments:
: C.I. Pigment Orange 61;
: C.I. Pigment Red 257 and 260;
: C.I. Pigment Yellow 109, 110, 173 and 185;

metal complex pigments:
: C.I. Pigment Yellow 117 and 153;

perinone pigments:
: C.I. Pigment Orange 43;
: C.I. Pigment Red 194;

perylene pigments:
: C.I. Pigment Black 31 and 32;
: C.I. Pigment Red 123, 149, 178, 179, 190 and 224;
: C.I. Pigment Violet 29;

phthalocyanine pigments:
: C.I. Pigment Blue 15, 15:1, 15:2, 15:3, 15:4, 15:6 and 16;
: C.I. Pigment Green 7 and 36;

pyranthrone pigments:
: C.I. Pigment Orange 51;
: C.I. Pigment Red 216;

thioindigo pigments:
: C.I. Pigment Red 88;

triphenylmethane pigments:
: C.I. Pigment Blue 1, 61 and 62;
: C.I. Pigment Green 1;
: C.I. Pigment Red 81 and 169;
: C.I. Pigment Violet 2 and 3;

C.I. Pigment Black 1 (aniline black);

C.I. Pigment Yellow 101 (aldazine yellow); inorganic pigments:

white pigments:
: titanium dioxide (C.I. Pigment White 6), zinc white, paint zinc oxide; zinc sulfide, lithopones; lead white;

black pigments:
: iron oxide black (C.I. Pigment Black 11), iron-manganese black, spinel black (C.I. Pigment Black 27); carbon black (C.I. Pigment Black 7);

color pigments:
: chromium oxide, chromium oxide hydrate green; chromium green (C.I. Pigment Green 48); cobalt green (C.I. Pigment Green 50); ultramarine green;
: cobalt blue (C.I. Pigment Blue 28 and 36); ultramarine blue; iron blue (C.I. Pigment Blue 27); manganese blue;
: ultramarine violet; cobalt violet and manganese violet;
: iron oxide red (C.I. Pigment Red 101); cadmium sulfoselenide (C.I. Pigment Red 108); molybdate red (C.I. Pigment Red 104); ultramarine red;
: iron oxide brown, mixed brown, spinel phases and corundum phases (C.I. Pigment Brown 24, 29 and 31), chromium orange; iron oxide yellow (C.I. Pigment Yellow 42); nickel-titanium yellow (C.I. Pigment Yellow 53; C.I. Pigment Yellow 157 and 164); chromium-titanium yellow; cadmium sulfide and cadmium zinc sulfide (C.I. Pigment Yellow 37 and 35); chromium yellow (C.I. Pigment Yellow 34), zinc yellow, alkaline earth metal chromates; Naples yellow; bismuth vanadate (C.I. Pigment Yellow 184);

luster pigments:
: metallic pigments based on metal oxide-coated metal plates; pearl luster (pearlescent) pigments based on metal oxide-coated mica platelets.

Dispersions of solids, especially pigment dispersions for varnishes, printing inks and paints in particular, using the novel phosphoric esters or mixtures thereof as dispersants, can be prepared in a variety of ways by methods known per se. In these methods, the critical requirement is to obtain a degree of mixing of pigment and dispersant which is as uniform as possible, and preferably to obtain covering of the surface of the pigment particles with the dispersant.

Thus the novel phosphoric esters, which depending on their composition are obtained in liquid or solid form as oils, waxes or pastes, are first of all dissolved, emulsified or suspended in any dispersion medium appropriate for the particular application. Dispersion media which are suitable in principle in this context are water, and organic solvents which are homogeneously miscible with or largely soluble in water. The pigment to be dispersed can then be added as a solid, in the form of a water-containing filter cake or as a slurry, likewise in any desired dispersion medium. The resulting dispersion is then thoroughly mixed, for example by stirring or shaking (with the addition if desired of dispersion auxiliaries such as glass beads or ceramic beads) or subjected to treatment with dispersing equipment such as ball mills.

Of course it is also possible to proceed in reverse and to add the phosphoric esters (as such or in dissolved, emulsified or dispersed form) to a slurry or dispersion of the pigment and then to carry out subsequent dispersion if appropriate and desired.

The resulting dispersions, comprising phosphoric ester, pigment and dispersion medium, can then be admixed, in order to produce waterborne, conventional or high-solids coating systems or printing inks, with further customary components such as binders (natural or synthetic resins, for example alkyd or acrylate resins, and also crosslinking agents and crosslinking catalysts if desired), leveling agents, thickeners and/or siccatives in one or more steps, or, conversely, the dispersion can also be added first of all to one or more of said components.

The dispersion medium can also be removed from the dispersions, largely or completely, by distillation or filtration, and the pigment "residue", which is dispersible as a result of its dispersant covering, can be employed for the desired purpose.

Other possibilities for the preparation of readily dispersible, liquid or preferably solid pigment preparations which are appropriate for the subsequent processing consist, for example, in adding the phosphoric ester at a later stage in the pigment synthesis or in mixing or milling isolated pigment and phosphoric ester in dry form, preferably with the aid of dispersion equipment.

Finally, pigment and phosphoric ester can also be employed directly, without mixing beforehand, in the preparation of varnishes, printing inks or paints.

A further option, especially in the context of the preparation of concentrate pastes for printing inks, is to add the phosphoric ester to the water-containing pigment filter cake during the flushing process, the pigment receiving a lipophilic wetting, and a largely pigment-free aqueous phase being deposited.

With the aid of the novel phosphoric esters it is possible to produce varnishes, printing inks or paints having outstanding performance properties (high flocculation stability, very good flow properties, good color properties, good gloss and high transparency). In this case, in general, from 0.1 to 30% by weight of phosphoric ester are used, preferably from 1 to 15% by weight, based on the pigment to be dispersed.

EXAMPLES

A) Preparation of novel phosphoric esters

Examples 1 to 11 a) Preparation of the amino (ether) alcohol (AEA)

This was prepared in a generally known manner by two-step reaction of amine and EO, using in the first stage 5% by weight of water based on the amine, as catalyst at from 130 to 150° C., and in the second stage from 1 to 2% by weight, based on the amine, of potassium tert-butanolate (Example 10: potassium hydroxide) as catalyst, at from 120 to 130° C.

b) Preparation of the amino (ether) ester (AEE)

A mixture of $X_b$ g of the amino (ether) alcohol (AEA) obtained in step a), $y_b$ g of $\epsilon$-caprolactone ($\epsilon$) and $z_b$ g of dibutyltin dilaurate (ZBL) was heated to $T_b°$ C. under inert gas, stirred at this temperature for $t_b$ h and then cooled to room temperature.

c) Preparation of the amino (ether) ester phosphate (AEEP)

Under inert gas and with the exclusion of moisture, $x_c$ g of the amino (ether) ester (AEE) obtained in step b) were heated with stirring at $T_c°$ C. Following the addition of $y_c$ g of phosphatizing agent P (polyphosphoric acid (85% $P_4O_{10}$)-PPA or phosphorus pentoxide ($P_4O_{10}$)), the mixture was stirred at this temperature for $t_c$ h and then cooled to room temperature.

Details regarding these experiments and their results are summarized in Tables 1a to 2c. The mean molecular weights $\bar{M}_n$ indicated therein were determined by way of the amine number. The viscosities $\eta$[mpas] likewise listed were measured using a Haake VT 500 rotary viscometer.

TABLE 1a

| Ex. | $x_a$ g | Amine A | $y_a$ g 1st step | EO 2st step | $\bar{M}_n$ |
|---|---|---|---|---|---|
| 1 | 240 | Di(2-ethylhexyl)amine | 50 | 320 | 540 |
| 2 | 180 | Dicyclohexylamine | 50 | — | |
| 3 | 180 | Dicyclohexylamine | 50 | 580 | 830 |
| 4 | 370 | Di(2-ethylhexyl)amine | 75 | 900 | 860 |
| 5 | 370 | Di(2-ethylhexyl)amine | 75 | 900 | 860 |
| 6 | 350 | N,N-Dibutylethanolamine* | — | 810 | 560 |
| 7 | 240 | Di(2-ethylhexyl)amine | 50 | 530 | 810 |
| 8 | 240 | Di(2-ethylhexyl)amine | 50 | 320 | 540 |
| 9 | 600 | N-Coconut fatty-1,3-diaminopropane | 320 | — | 370 |
| 10 | 100 | Polyethyleneimine ($\bar{M}_n$ = 750) | 110 | 320 | 3500 |
| 11 | — | Triethanolamine* | — | — | |

*The EO adduct alcohol amine was employed directly

TABLE 1b

| Ex. | $x_b$ g AEA | $y_b$ g $\epsilon$ | $z_b$ g ZBL | $T_b$ [° C.] | $t_b$ h | Yield [g] | Result Appearance | $\bar{M}_n$ | $\eta$ [mPas] |
|---|---|---|---|---|---|---|---|---|---|
| 1 | 150 | 87 | 0.2 | 135 | 5 | 133 | beige oil | 840 | 70[a] |
| 2 | 80 | 122 | — | 135 | 5 | 200 | clear brown liquid | 580 | 20[a] |
| 3 | 80 | 69 | — | 135 | 5 | 143 | light-colored wax | 1490 | 340[a] |
| 4 | 120 | 96 | 0.2 | 135 | 5 | 211 | light-colored wax | 1540 | 180[a] |
| 5 | 110 | 103 | 0.2 | 135 | 5 | 209 | light-colored wax | 1610 | 265[a] |
| 6 | 228 | 320 | 0.5 | 135 | 5 | 532 | beige paste | 1370 | 180[a] |
| 7 | 167 | 114 | — | 160 | 10 | 270 | orange-brown oil | 1490 | 135[a] |
| 8 | 89 | 86 | — | 160 | 10 | 165 | brown paste | 1090 | 125[a] |
| 9 | 97 | 143 | 0.2 | 130 | 4 | 233 | brown liquid | 1100 | 150[a] |
| 10 | 73 | 228 | 0.3 | 130 | 5 | 301 | light brown wax | 16000 | 1540[b] |
| 11 | 15 | 114 | 0.1 | 130 | 5 | 125 | light-colored solid | 1250 | 430[a] |

[a]Measurement with sensor NV at 50° C. and a shear rate D = 100 s$^{-1}$
[b]Measurement with sensor NV at 50° C. and a shear rate D = 40 s$^{-1}$ TABLE 1c

| Ex. | $x_c$ g AEE | $y_c$ g | P | $T_c$ [° C.] | $T_c$ h | Yield [g] | Result Appearance | $\eta$ [mPas] |
|---|---|---|---|---|---|---|---|---|
| 1 | 81 | 6.3 | $P_4O_{10}$ | 80 | 6 | 86 | beige oil of high viscosity | 3820[c] |
| 2 | 40 | 7.7 | PPA | 80 | 6 | 47 | brown wax | — |
| 3 | 59 | 4.4 | PPA | 80 | 6 | 63 | yellowish paste | 3200[c] |

TABLE 1c-continued

| Ex. | $x_c$ g AEE | $y_c$ g | P | $T_c$ [° C.] | $T_c$ h | Yield [g] | Result Appearance | η [mPas] |
|---|---|---|---|---|---|---|---|---|
| 4 | 50 | 3.4 | PPA | 80 | 6 | 53 | beige paste | 4180[c] |
| 5 | 50 | 3.2 | PPA | 80 | 6 | 53 | beige paste | 3260[c] |
| 6 | 110 | 13.2 | PPA | 80 | 7 | 163 | brown paste | 2450[c] |
| 7 | 141 | 4.8 | $P_4O_{10}$ | 80 | 6 | 144 | beige paste | 1380[c] |
| 8 | 116 | 4.8 | $P_4O_{10}$ | 80 | 6 | 120 | brown paste | 540[c] |
| 9 | 48 | 5.2 | PPA | 80 | 5 | 53 | brown wax | 35000[d] |
| 10 | 90 | 5.2 | PPA | 75 110 | 4 3 | 95 | brown wax | 88000[d] |
| 11 | 65 | 5.2 | PPA | 80 | 5 | 69 | brown wax | 11000[d] |

[c]Measurement with sensor PK 1.1° at 60° C. and a shear rate D = 400 s$^{-1}$
[d]Measurement with sensor PK 1.1° at 60° C. and a shear rate D = 40 s$^{-1}$ B) Use of novel phosphoric esters B1) Preparation of tinting pastes A mixture of in each case 1.5 g of the dispersant obtained in A), 13.5 g of C.I. Pigment Red 101 (mean particle size <0.1 μm) and 20.0 g of water was made into a paste by treatment in a dissolver for 10 minutes. Following addition of 61.7 g of an aqueous anionic polyurethane dispersion, setting of a pH of 7.8 by addition of 10% strength aqueous dimethylethanolamine solution, and making up with water to 100 g, the mixture was triturated in a Skandex with 240 g of SAZ beads (diameter about 1.5 mm) for 120 minutes.

B2) Testing

Color strength:

The color strength (given as color equivalents FAE) was determined in accordance with DIN 53 234 by way of the whitened form of the respective tinting paste using a white paint. For this purpose, 2.0 g of tinting paste were mixed with 4.0 g of a white paint pigmented with 38.8% by weight of $TiO_2$.

The analogous preparation with the uncoated pigment was given the FAE value 100 (standard). FAE values <100 denote a higher color strength than that of the standard, while, correspondingly, FAE values >100 denote a lower color strength.

Gloss:

The gloss was determined in accordance with DIN 67 530, measuring a 36 μcoating of the respective tinting paste, drawn out with a doctor blade onto acetate film and baked at 90° C. for 10 minutes, using the Byk Multigloss gloss meter at a measurement angle of 20°.

Transparency:

The transparency was determined in accordance with DIN 55 988, by evaluating a 150 μcoating of the respective tinting paste, drawn out with a doctor blade onto a metal contrast sheet and baked at 90° C. for 10 minutes, visually in accordance with a scale of ±5 steps:+5=markedly more transparent;+4=more transparent;+3=somewhat more transparent; +2=slightly more transparent;+1=a touch more transparent; 0=standard (tinting materials with uncoated pigment);-1=a touch more opaque;-2=a slightly more opaque;-3=somewhat more opaque;-4=more opaque;-5= markedly more opaque.

Flow properties:

The flow properties of the respective tinting paste were determined qualitatively in accordance with the DIN cup measurement, employing 5 grades (5=very runny←1=non-flowing).

Rubout (flocculation, floating):

The rubout was determined in accordance with DIN ISO 8781, using as a measure of the flocculation the rub-out number (RN) which results in accordance with the following formula from the color strength $F_n$ of a normally applied coating of the above-described whitened tinting paste and from the color strength $F_g$ of a coating which is rubbed before initial drying:

$RN = (F_g/F_n - 1) \times 100$

The further the numerical distance between the rub-out number and zero (=no differences in color strength), the greater the degree of flocculation in the coating material (RN >0: flocculation of the color pigment, the rubbed area appears darker or more colored; RN <0: flocculation of the white pigment, the rubbed area appears lighter).

The test results are compiled in the table below.

TABLE

| Testing of the dispersant from Example | Color strength FAE value | Gloss | Transparency Grade | Flow properties Grade | Rubout RN |
|---|---|---|---|---|---|
| 1 | 94 | 105 | +5 | 4 | +5 |
| 2 | 90 | 109 | +5 | 4 | -2 |
| 3 | 101 | 75 | +3 | 5 | +5 |
| 4 | 91 | 118 | +4 | 3 | 0 |
| 5 | 97 | 107 | +4 | 4 | +2 |
| 6 | 99 | 69 | +3 | 5 | +10 |
| 7 | 104 | 115 | +3 | 3 | 0 |
| 8 | 104 | 117 | +3 | 3 | +1 |
| 9 | 98 | 115 | +5 | 3–4 | +3 |
| 10 | 97 | 114 | +5 | 3 | +12 |
| 11 | 100 | 72 | +(3–4) | 5 | +5 |

We claim:

1. A phosphoric ester which is obtained by the process of:
 a) reacting (1) ammonia, or a primary or secondary amine, said amine being a mono-oligo-, or polyamine, with (2) a $C_2$–$C_8$ alkylene oxide, styrene oxide, or $C_2$–$C_8$ alkylene carbonate to give (3) an amino (ether) alcohol which is an amino alcohol, an amino mono-, oligo- or polyether alcohol, 100% of the alkoxylatable NH groups of the amine being alkoxylated,
 b) reacting the resulting amino (ether) alcohol (3) with (4A) a hydroxycarboxylic acid or ester thereof, to give (5A) a mono-, oligo- or polyester, from 50 to 100% of the terminal hydroxyl groups in the amino (ether) alcohol being esterified, and
 c) reacting the resulting amino (ether) ester (5A) with (6) a phosphorous compound which forms phosphoric esters, from 5 to 100% of the terminal hydroxyl groups in the amino (ether) ester (5A) being converted into phosphoric ester groups, and the phosphorous atoms being mono-, di-, and/or tri-esterified.

2. A phosphoric ester as claimed in claim 1, which contains from 1 to 200 alkylene oxide units per alkoxylatable amino hydrogen present in component (1).

3. A phosphoric ester as claimed in claim 1, which contains from 1 to 150 carboxylic ester groups per alkoxylatable amino hydrogen present in component (1).

4. A phosphoric ester as claimed in claim 1, which contains from 0.05 to 3 phosphorus atoms per alkoxylatable amino hydrogen present in component (1).

5. A phosphoric ester as claimed in claim 1, in which terminal hydroxyl groups of the amino (ether) alcohol (3) are completely esterified.

6. A phosphoric ester as claimed in claim 1, in which terminal hydroxyl groups of the amino (ether) ester (5A) are completely converted into phosphoric ester groups.

7. A phosphoric ester as claimed in claim 1, in which the OH functions of a less than tri-esterified phosphorus atom are in acid or salt form.

8. A process for the preparation of a phosphoric ester, which comprises:
   a) reacting (1) ammonia, or a primary or secondary amine, said amine being a mono-oligo-, or polyamine, with (2) a $C_2$–$C_8$ alkylene oxide, styrene oxide, or $C_2$–$C_8$ alkylene carbonate to give (3) an amino (ether) alcohol which is an amino alcohol, an amino mono-, oligo- or polyether alcohol, 100% of the alkoxylatable NH groups of the amine being alkoxylated,
   b) reacting the resulting amino (ether) alcohol (3) with (4A) a hydroxycarboxylic acid or ester thereof, to give (5A) a mono-, oligo- or polyester, from 50 to 100% of the terminal hydroxyl groups in the amino (ether) alcohol being esterified, and
   c) reacting the resulting amino (ether) ester (5A) with (6) a phosphorous compound which forms phosphoric esters, from 5 to 100% of the terminal hydroxyl groups in the amino (ether) ester (5A) being converted into phosphoric ester groups, and the phosphorous atoms being mono-, di-, and/or tri-esterified.

9. The process as claimed in claim 8, wherein step b), an ester of the hydroxycarboxylic acid is employed.

10. A method for dispersing solids in plastics, varnishes, printing inks and paints which comprises using a phosphoric ester as claimed in claim 1 as dispersant.

11. A phosphoric ester which is obtained by the process of:
   b) reacting an amino (ether) alcohol which is an amino alcohol, an amino ether alcohol or a polyamino polyether alcohol, wherein said alcohol contains only tertiary nitrogen atoms, with (4A) a hydroxycarboxylic acid or ester thereof, to give (5A) a mono-, oligo- or polyester, from 50 to 100% of the terminal hydroxyl groups in the amino (ether) alcohol being esterified, and
   c) reacting the resulting amino (ether) ester (5A) with (6) a phosphorous compound which forms phosphoric esters, from 5 to 100% of the terminal hydroxyl groups in the amino (ether) ester (5A) being converted into phosphoric ester groups, and the phosphorous atoms being mono-, di-, and/or tri-esterified.

12. A process for preparing a phosphoric ester, which comprises
   b) reacting an amino (ether) alcohol which is an amino alcohol, an amino ether alcohol or a polyamino polyether alcohol, wherein said alcohol contains only tertiary nitrogen atoms, with (4A) a hydroxycarboxylic acid or ester thereof, to give (5A) a mono-, oligo- or polyester, from 50 to 100% of the terminal hydroxyl groups in the amino (ether) alcohol being esterified, and
   c) reacting the resulting amino (ether) ester (5A) with (6) a phosphorous compound which forms phosphoric esters, from 5 to 100% of the terminal hydroxyl groups in the amino (ether) ester (5A) being converted into phosphoric ester groups, and the phosphorous atoms being mono-, di-, and/or tri-esterified.

* * * * *